United States Patent
Wang et al.

(10) Patent No.: US 10,086,067 B2
(45) Date of Patent: Oct. 2, 2018

(54) PHARMACEUTICAL COMPOSITION FOR VIRAL IMMUNOTHERAPY AND USES THEREOF

(71) Applicant: Fudan University, Shanghai (CN)

(72) Inventors: Bin Wang, Shanghai (CN); Xianzheng Wang, Shanghai (CN); Jiming Zhang, Shanghai (CN)

(73) Assignee: Fudan University, Shanghai (CN)

( * ) Notice: Subject to any disclaimer, the term of this patent is extended or adjusted under 35 U.S.C. 154(b) by 21 days.

(21) Appl. No.: 15/007,160

(22) Filed: Jan. 26, 2016

(65) Prior Publication Data

US 2016/0136265 A1 May 19, 2016

Related U.S. Application Data

(63) Continuation-in-part of application No. PCT/CN2014/000717, filed on Jul. 28, 2014.

(30) Foreign Application Priority Data

Jul. 26, 2013 (CN) .......................... 2013 1 0322617

(51) Int. Cl.
| | |
|---|---|
| *A61K 39/29* | (2006.01) |
| *A61K 39/39* | (2006.01) |
| *A61K 38/19* | (2006.01) |
| *A61K 38/21* | (2006.01) |
| *A61K 47/48* | (2006.01) |
| *A61K 31/513* | (2006.01) |
| *A61K 31/522* | (2006.01) |
| *A61K 31/675* | (2006.01) |
| *A61K 31/7072* | (2006.01) |
| *A61K 45/06* | (2006.01) |
| *A61K 39/12* | (2006.01) |
| *C12N 7/00* | (2006.01) |
| *A61K 39/00* | (2006.01) |

(52) U.S. Cl.
CPC .......... *A61K 39/292* (2013.01); *A61K 31/513* (2013.01); *A61K 31/522* (2013.01); *A61K 31/675* (2013.01); *A61K 31/7072* (2013.01); *A61K 38/193* (2013.01); *A61K 38/21* (2013.01); *A61K 38/212* (2013.01); *A61K 39/12* (2013.01); *A61K 39/39* (2013.01); *A61K 45/06* (2013.01); *A61K 47/48215* (2013.01); *C12N 7/00* (2013.01); *A61K 2039/545* (2013.01); *A61K 2039/55522* (2013.01); *C12N 2730/10134* (2013.01)

(58) Field of Classification Search
None
See application file for complete search history.

(56) References Cited

FOREIGN PATENT DOCUMENTS

| CN | 1990043 A | 7/2007 |
|---|---|---|
| CN | 101509008 A | 8/2009 |

OTHER PUBLICATIONS

NCT0187856. The Treatment With HBIG+GM-CSF+HBV Vaccine for Chronic Hepatitis B Patients With HBeAg Seroconversion. Dated Jun. 12, 2013.*
Wang et al. A pilot study on the combined therapy of granulocyte-macrophage colonystimulating factor and hepatitis B vaccine on chronic hepatitis B virus carrier children. Chinese Medical Journal 2002; 115( 12 ) : 1824-1828.*
Xu et al. Results of a phase III clinical trial with an HBsAg-HBIG immunogenic complex therapeutic vaccine for chronic hepatitis B patients: Experiences and findings. Journal of Hepatology 2013 vol. 59: 450-456.*
Perrillo et al. Benefits and risks of interferon therapy for hepatitis B. Hepatology. May 2009;49(5 Suppl):S103-11.*
Michel et al. Therapeutic vaccines and immune-based therapies for the treatment of chronic hepatitis B: Perspectives and challenges. Journal of Hepatology 2011, 54: 1286-1296.*
Lin et al. Effect of GM-CSF in combination with hepatitis B vaccine on revacination of healthy adult non-responders. Journal of Infection (2010) 60, 264e270.*
"ISR of PCT CN2014/000717".
Zhang, Yijun; "Comments on Antiviral Treatment of Chronic Hepatitis B", Infectious Disease Information, vol. 15, No. 3, pp. 102-103.
Feng, Li et al., "Progress in the Developments of Hepatitis B Vaccine and its Adjuvants", Chinese Journal of New Drugs, vol. 16, No. 20, pp. 1660-1665.
Ding, Fengying; "Clinical Observation on Combination Therapy of Interferon-☐1b and Hepatitis B Gene Vaccine for Chronic Hepatitis B in 40 cases", Shandong Medical Journal, vol. 42, No. 30, pp. 45-46.
Zhang, Junxin et al., "Combination Therapy of Lamivudine and Hepatitis B Vaccine for Chronic Hepatitis B: an Analysis of 39 Cases", World Chinese Journal of Digestology, vol. 17, No. 6, pp. 614-617.
Wu, Xiuying et al., "Curative Effect Observation on Combination Therapy of Lamivudine and Hepatitis B Vaccine for Chronic Hepatitis B", The Medical Journal of Industrial Enterprise, vol. 17, No. 5, pp. 17-18.
Hou, Jinlin, Wei Lai, "Guideline for Prevention and Treatment of Chronic Hepatitis", Chinese Journal of the Frontiers of Medical Science, 2011, vol. 3, No. 1, pp. 66-82.

(Continued)

*Primary Examiner* — Nianxiang Zou
(74) *Attorney, Agent, or Firm* — Quarles & Brady LLP

(57) ABSTRACT

The present disclosure relates to a method of overcoming host immune tolerance in a subject having chronic hepatitis B virus (HBV) infection, comprising administering to the subject an immunomodulatory agent and a recombinant HBV vaccine, such that the immune tolerance of the chronic HBV infection in the subject is overcome. Moreover, the present disclosure relates to a method of treating chronic HBV infection in a subject in need thereof, comprising administering to the subject a first anti-viral agent, an immunomodulatory agent and a recombinant hepatitis B vaccine, such that the HBV infection in the subject is treated.

16 Claims, 4 Drawing Sheets

(56) References Cited

OTHER PUBLICATIONS van de Laar L, Coffer P, Woltman A: Regulation of dendritic cell development by GM-CSF: molecular control and implications for immune homeostasis and therapy. Blood 2012, 119(15):3383-3393.
Wanjalla C, Goldstein E, Wirblich C, Schnell M: A role for granulocyte-macrophage colony-stimulating factor in the regulation of CD8(+) T cell responses to rabies virus. Virology 2012, 426(2):120-133.
Cytokines as natural adjuvants for vaccines.pdf.
Cruciani M, Mengoli C, Serpelloni G, Mazzi R, Bosco O, Malena M: Granulocyte macrophage colony-stimulating factor as an adjuvant for hepatitis B vaccination: a meta-analysis. Vaccine 2007, 25(4):709-718.
Morrey J, Bailey K, Korba B, Sidwell R: Utilization of transgenic mice replicating high levels of hepatitis B virus for antiviral evaluation of lamivudine. Antiviral research 1999, 42(2):97-108.
Paul N, Han S-H: Combination Therapy for Chronic Hepatitis B: Current Indications. Current hepatitis reports 2011, 10(2):98-105.
Rajkumar CG, Varsha T, Seyed NK, Shiv KS: Efficacy of granulocyte-macrophage colony-stimulating factor or lamivudine combination with recombinant interferon in non-responders to interferon in hepatitis B virus-related chronic liver disease patients. Journal of Gastroenterology and Hepatology 2002, 17, pp. 765-771.
GM-CSF as a Systemic Adjuvant in a Phase II Prostate Cancer Vaccine Trial.pdf.
Li Haiying et al.: "Synthesized Therapy of Interferon 1b Lamivudine, Hepatitis B Viral Vaccine and Vaccae in Patients with Chronic Hepatitis B" Journal of Clinical Hepatology, vol. 9 No. 4, Aug. 1, 2006, pp. 228-230.
D. H. Thiel et al. "A Preliminary Experience with GM-CSF Plus Interferon in Patients with HBV and HCV Resistant to Interferon Therapy" Journal of Viral Hepatitis, vol. 4 No. s1, Sep. 1, 1997, pp. 101-106.
Supplementary European Search Report issued in corresponding European Patent Application No. 14 82 9818, dated Mar. 20, 2017, 8 pages.
Ishikawa Tetsuya et al., "Combination therapy with Lamivudine and HB vaccine on chronic hepatitis B," Hepatology Research, vol. 37, Issue s1, Jul. 9, 2007, S62-S66 (5 pages), The Japan Society of Hepatology.

* cited by examiner

PHARMACEUTICAL COMPOSITION FOR VIRAL IMMUNOTHERAPY AND USES THEREOF

TECHNICAL FIELD

The present disclosure belongs to the biomedicine field, and relates to a new type of pharmaceutical composition for viral immunotherapy, particularly relates to a pharmaceutical composition for viral immunotherapy used to treat persistent hepatitis B virus infection.

BACKGROUND

The existing technology relates to hepatitis B, an infectious disease caused by hepatitis B virus (HBV) infection, transmitted by blood and body fluid, and characterized by liver damage, which is a serious problem to public health and a great threat to human health. Studies show that some of the patients infected with hepatitis B will develop into a state of chronically persistent infection, which may convert to cirrhosis or primary hepatocellular carcinoma (HCC). China is the high epidemic region of hepatitis B virus infections. 0.35 million people die from hepatitis B associated diseases (such as cirrhosis, HCC etc.) each year, in which the infection rate in the population is 60%, and the carrier rate of the hepatitis B surface antigen (HBsAg) in the population is 10%. Currently, it is estimated that there are about 300 million HBsAg carriers globally, ⅓ of whom living in China. Therefore, the transmission of hepatitis B has become an important issue affecting the population quality in China.

It is shown in practice that hepatitis B vaccination is the best way to control or prevent hepatitis B. The genetically recombinant hepatitis B vaccine has been developed rapidly since 1980s. Since 1981, Merck has successfully developed and commercialized the recombinant vaccine with hepatitis B gene S protein expressed in yeast and used with Alum adjuvant, and has played an important role in preventing and controlling hepatitis B globally. Currently, most marketed hepatitis B vaccines are based on hepatitis B viral S antigen used with Alum adjuvant.

For chronic hepatitis B (CHB) patients, persistent HBV replications in hepatocyte will cause the exhaustion of the virus-specific T cell in the body and the immune escape of the virus, which will lead to immune tolerance of the patients, and weaken the function of virus-specific CTL. Studies have demonstrated that the low response of HBV specific T cell may be one of the most important reasons for the persistent infection of HBV, the specific molecular mechanism of which is still unknown. It is anticipated that it might be associated with load of virus antigen, efficiency of innate immunity, type of antigen present cells, quantity and function of T helper cell and regulatory T cells, and regulation of costimulatory molecules.

According to the Guideline for Prevention and Treatment of Chronic Hepatitis published by Chinese Medical Association of liver diseases and infectious diseases, the HBV patients who are suitable for anti-virus agent treatments should be provided with antiviral treatment. Antiviral agents against hepatitis B currently include alpha interferon (α-IFN) and nucleos(t)ide analogues such as lamivudine, adefovir, entecavir, telbivudine, tenofovir etc., which can inhibit the copy number of HBV DNA in patients within the scope of indication, but are easy to develop drug resistance upon long-term administration. Moreover, the discontinuation of nucleos(t)ide analogues administration will lead to reoccurrence even exacerbation of the disease. Long-term administration of interferon will lead to significant side effects due to its bone marrow suppression effects. Formulations of Glycyrrhizin, Silymarin, polyunsaturated lecithin and bicyclol all have effects on anti-inflammation, anti-oxidation, protection of hepatocyte membrane and organelles in different levels, and it is shown by clinical trial results that they can improve the biochemical index of liver, but cannot replace anti-virus therapies.

Currently researchers believe that the effective immunotherapy should rely on stimulating immune system of hepatitis B carriers. It is known that Granulocyte-macrophage colony stimulating factor (GM-CSF) is a type of important growth factor of hematopoietic cells with multiple potentials, and has a significant curative effect on leukopenia caused by various reasons. GM-CSF, mainly produced by activated T cells, B cells, macrophage, mast cells, endothelial cells and fibroblasts, can not only promote proliferation, differentiation and maturation of hematopoietic precursors, but also have different levels of stimulating effects on other cells such as antigen presenting cell (APC), fibroblasts, keratinocytes, skin mucous cells. etc. In 1993, Dranoff et al. used GM-CSF as an immune adjuvant to enhance immune response of cancer vaccine for the first time. The enhanced immune effects of GM-CSF may rely on the enhanced ability of antigen presentation by APC. When interacting with Dendritic Cells (DC), GM-CSF can promote antigen presentation [1], increase IL-2 production, activate CD4+ T cells, increase the ability of antibody secreting and enhance the function of CD8+ T cells [2]. Recent investigations indicated that GM-CSF can activate T cells and endothelia, enhance the function of APC, upregulate molecular MHC, costimulate molecules, participate immune modulation of organism, and enhance the therapeutic effects of antiviral agents. However, Hasan et al. discovered that GM-CSF did not provide significant adjuvant activity, i.e. it could not effectively enhance primary immune response, when it was intramuscularly injected immediately before the injection of recombinant hepatitis B vaccine in normal individual [3]. V. Bronte found that systemic high level of GM-CSF can induce transient T cells suppression [4]. In a phase II clinical trial for prostate cancer vaccine, S. J. Simmons et al. used GM-CSF as systemic adjuvant, but could not detect the enhanced clinical responses after the injection of DC-polypeptide or significantly enhanced immune responses. Moreover, the dose related side effects such as local reactions, fatigue, bone pain, myalgia and fever occurred in some patients [5]. Such results are different from some other reports in which GM-SCF acting as immune adjuvant could significant enhance antigen specific immune responses, which indicates that the doses, administration duration, and immune dose of GM-CSF are closely related to clinical immune results. However, the studies on dose and duration of GM-CSF immunotherapy are not thorough, and it is necessary to perform systematic studies to optimize the administration protocol of GM-CSF as immunotherapy agent.

It has been reported that using interferon alone as treatment for HBV could achieve about 25%-40% of efficacy. Lamivudine is still the primary choice as treatment for HBV infection in most regions due to its relative safety and low price, although the rapidly developed drug resistance is the main drawback [6]. As the usage of adefovir increases, the drug resistance to such agent has become a major problem, which indicates that some patients do not respond to the mono-agent therapy, or are easy to develop drug resistance. Given the successful combinational therapy against HIV infections and the various problems associated with mono-agent therapy against HBV, more researchers began to study combinational therapy against HBV [7]. When conducting combination therapy with GM-CSF and interferon, Guptan et al. observed that 60% of the HBV patients, who did not respond to the interferon monotherapy, had a decreased level of HBeAg and HBV-DNA at the end of the initial combination therapy, but some of the patients showed recurrences of the virus [8]. While after six months' combination therapy with interferon and hepatitis B vaccine, Heintges et al. observed that 50% (8/19) of the individuals, who did not respond to interferon monotherapy, showed undetectable HBV-DNA level, but the sustained response rate after the therapy was not reported in the clinical trial. Some studies reported that by direct treatment with HBsAg vaccination, 28.6% of the virus carriers had reduced level of virus replications and 21.4% of the virus carriers had negative HBV-DNA. However, Dikici et al. found that there was no significant difference between the hepatitis B vaccinated group and the unvaccinated group of the chronic HBV infected children with immune resistance.

The Chinese publication CN 1990043A "Application of recombinant human granulocyte macrophage colony stimulating factor in the treatment or prevention of hepatitis B virus" disclosed the combination administration of recombinant human GM-CSF and genetically engineered Hepatitis B vaccine can enhance humoral immune response of organism. The administration of recombinant human GM-CSF before genetically engineered HBsAg vaccination can stimulate the cellular immunity in animals, promote T cell differentiation, stimulate the secretion of cellular factors such as IFN-γ and the like in Th1 cell, increase the production of IgG2a antibody, and enhance the function of cytotoxic T cells (CTL), so that a treating efficacy for HBV is achieved. In recent years, different kinds of cytokines and chemokines have been used as the immune adjuvant for the studies of animal models and human vaccines to promote antigen recognition and T cell proliferation. It is also reported that GM-CSF is currently the most used cytokine adjuvant in terms of increasing the immunogenicity of cancer vaccines. GM-CSF can release the cytokine by genetic transducing into tumor cells or to surrounding normal cells. In addition, GM-CSF can be used locally or systemically for different vaccinations on animals or patients administered with the form of recombinant protein. However, it is still under argument whether GM-CSF should be used as an immune adjuvant for anti-virus vaccine in human. By intramuscularly injecting GM-CSF immediately before the injection of recombined hepatitis B vaccine into normal individual, Hasan et al. found that GM-CSF cannot provide significant adjuvant activities, which indicates it cannot enhance primary immune responses effectively [3]. The difference in results by using the same GM-CSF as adjuvant may relate to the dose, injection site and method of immunization in actual application.

Based on the studies listed above, the inventors of the present application propose to provide a new pharmaceutical composition for viral immunotherapy, especially a pharmaceutical composition for viral immunotherapy for persistent hepatitis B infection.

The existing techniques associated with the present disclosure are:

1. van de Laar L, Coffer P, Woltman A: Regulation of dendritic cell development by GM-CSF: molecular control and implications for immune homeostasis and therapy. Blood 2012, 119(15):3383-3393.

2. Wanjalla C, Goldstein E, Wirblich C, Schnell M: A role for granulocyte-macrophage colony-stimulating factor in the regulation of CD8(+) T cell responses to rabies virus. Virology 2012, 426(2):120-133.

3. Cruciani M, Mengoli C, Serpelloni Mazzi R, Bosco O, Malena M: Granulocyte macrophage colony-stimulating factor as an adjuvant for hepatitis B vaccination: a meta-analysis. Vaccine 2007, 25(4):709-718.

4. Paola Rizza, Maria Ferrantini, Imerio Capone, Filippo Belardelli: Cytokines as natural adjuvants for vaccines: where are we now. Trends in Immunology, 2002, Vol. 23, No. 8, 381-383.

5. S. J. Simmons, B. A. Tjoa, M. Rogers, A. Elgamal, G M. Kenny, H. Ragde, M. J. Troychak, A. L. Boynton, G P. Murphy, GM-CSF as a Systemic Adjuvant in a Phase II Prostate Cancer Vaccine Trial. The Prostate, 1999, 39:291-297.

6. Morrey J, Bailey K, Korba B, Sidwell R: Utilization of transgenic mice replicating high levels of hepatitis B virus for antiviral evaluation of lamivudine. Antiviral research 1999, 42(2):97-108.

7. Paul N, Han S-H: Combination Therapy for Chronic Hepatitis B: Current Indications. Current hepatitis reports 2011, 10(2):98-105.

8. Rajkumar C G, Varsha T, Seyed N K, Shiv K S: Efficacy of granulocyte-macrophage colony-stimulating factor or lamivudine combination with recombinant interferon in non-responders to interferon in hepatitis B virus-related chronic liver disease patients. Journal of Gastroenterology and Hepatology 2002, 17.

SUMMARY

The purpose of this disclosure is to provide a new pharmaceutical composition for viral immunotherapy, which especially relates to a pharmaceutical composition for viral immunotherapy for persistent hepatitis B infection. The pharmaceutical composition in present disclosure can provide a new immunotherapy for treatment of hepatitis B.

In one aspect, the present disclosure provides methods of overcoming host immune tolerance in a subject having hepatitis B virus (HBV) infection, comprising administering to the subject an immunomodulatory agent and a recombinant HBV vaccine, such that the immune tolerance of the chronic HBV infection in the subject is overcome.

In another aspect, the present disclosure provides methods of treating HBV infection in a subject in need thereof, comprising administering to the subject a first antiviral agent, an immunomodulatory agent and a recombinant hepatitis B vaccine, such that the HBV infection in the subject is treated.

In certain embodiments, the present disclosure provides a pharmaceutical composition consisting of an antiviral agent, an immunomodulatory agent and a recombinant hepatitis B vaccine.

In certain embodiments, the pharmaceutical composition can be used for treatment of hepatitis B, especially suitable for treatment of chronic hepatitis B. In the pharmaceutical composition as described, antiviral agents such as α-IFN, nucleos(t)ide analogues and the like are used to lower virus load in organism, followed by administration of hepatitis B vaccine with GM-CSF as an adjuvant, to establish effective immune memory protective reaction in organism, to produce strong antibody protection and cellular immunity, to prevent recurrence of virus, even to achieve the elimination of viruses, and to prevent HBV re-infection.

In certain embodiments, the antiviral agent is selected from interferon or nucleos(t)ide analogues, such as IFN-α 3~5 MU, PEG-IFN-α 2a, PEG-IFN-α 2b, lamivudine (LAM), adefovir dipivoxil (ADV), entecavir (ETV), telbivudine (LdT), tenofovir disoproxil fumarate (TDF).

In certain embodiments, the immunomodulatory agent is selected from recombinant human granulocyte macrophage colony stimulating factor, such as GM-CSF.

In certain embodiments, the recombinant hepatitis B vaccine is genetically engineered hepatitis B vaccine, such as subunit protein vaccine, or a therapeutic HBV vaccine.

In certain embodiments, the following techniques and methods are adopted. Genetic engineering technique is used to express interferon gene in *Escherichia coli* or yeast system to get protein, which is then purified and formulated with adjuvants to make antiviral agent IFN-α (interferon type I); genetic engineering technique is used to express recombinant human granulocyte macrophage colony stimulating factor gene in yeast system to get protein, which is purified and formulated with adjuvants to make immunomodulatory agent rhGM-CSF (recombinant human granulocyte macrophage colony stimulating factor); genetic engineering technique is used to express hepatitis B antigen gene of human in yeast system to get protein, which is purified and formulated with adjuvants to make recombinant hepatitis B surface antigen vaccine.

In certain embodiments, the interferon and nucleos(t)ide analogues in the pharmaceutical composition of present disclosure are all commercially used as antiviral agents.

In certain embodiments, in the pharmaceutical composition of present disclosure, the amount of the antiviral agent is the dosage conventionally used in clinic, which can refer to the Guideline of Prevention and Treatment of Chronic Hepatitis; the weight ratio of the genetically engineered hepatitis B vaccine to the recombinant human granulocyte macrophage colony stimulating factor is 1:1-30.

In certain embodiments, the dosage and the use of the antiviral agent can refer to the Guideline of Prevention and Treatment of Chronic Hepatitis, such as:

1. 3~5 MU common IFN-α, which can be adjusted depending on the tolerance of patient, is subcutaneously injected 3 times per week or every other day for 6 months.

2. 180 μg polyethylene glycol-IFN-α 2a is subcutaneously injected once per week for one year.

3. 1.0~1.5 μg/kg polyethylene glycol-IFN-α 2b is subcutaneously injected once per week for one year.

4. Lamivudine (LAM): 100 mg lamivudine is orally administered once daily.

5. Adefovir dipivoxil (ADV): 10 mg adefovir dipivoxil is orally administered once daily.

6. Entecavir (ETV): 0.5 mg entecavir is orally administered once daily.

7. Telbivudine (LdT): 600 mg telbivudine is orally administered once daily.

8. Tenofovir disoproxil fumarate (TDF): TDF (which has not yet been approved in China) has a similar structure as adefovir dipivoxil but is less toxic to kidney, the therapeutic dose is 300 mg daily.

The antiviral agent, immunomodulatory agent, and HBV vaccine in the pharmaceutical composition of the present disclosure are suitable for administration as a mixture or in a separate manner, wherein the administration is via subcutaneous or intramuscular injection, or via oral administration in combination with injection respectively, or at different times in different order.

For example, the antiviral agent can be administered prior to the administration of the genetically engineered hepatitis B vaccine, or the recombinant human granulocyte macrophage colony stimulating factor can be administered prior to the administration of genetically engineered hepatitis B vaccine.

Specifically, in another aspect, the present disclosure discloses the use of the antiviral agent (interferon and nucleos(t)ide analogues, etc.), immunomodulatory agent (recombinant human granulocyte macrophage colony stimulating factor) and recombinant hepatitis B Vaccine for treating hepatitis B, especially the use thereof in the manufacture of a medication for treating chronic hepatitis B.

In certain embodiments, the antiviral agent can be administered prior to the administration of genetically engineered hepatitis B vaccine.

In certain embodiments, the recombinant human granulocyte macrophage colony stimulating factor can be administered prior to the administration of genetically engineered HBV vaccine.

The Guideline of Prevention and Treatment of Chronic Hepatitis can be referred to for the dosage of antiviral agents; the weight ratio of the genetically engineered recombinant hepatitis B vaccine to the recombinant human granulocyte macrophage colony stimulating factor is 1:1-30.

The pharmaceutical composition in present disclosure has been used in anti-virus immune experiments, the results of which show that α-IFN and nucleos(t)ide analogues can lower the virus load when the pharmaceutical composition is used to treat persistent hepatitis B infection. Hepatitis B vaccine using cytokine having an immune enhancement effect such as GM-CSF as adjuvant can enhance immune responses, help the organism to establish effective immune memory protective reaction, produce strong antibody protection and cellular immunity, clear virus, and prevent infections. In one embodiment of the present disclosure, a large number of experiments are performed using different immune combinations of recombinant human granulocyte macrophage colony stimulating factor and genetically engineered recombinant hepatitis B vaccine, the results of which show that in situ injection of recombinant human granulocyte macrophage colony stimulating factor (2-30 μg per animal per day) three days before the injection of hepatitis B vaccine, followed by genetically engineered hepatitis B vaccination (1 μg per animal), can effectively promote the maturation of dendritic cells of animals, significantly increase the cellular immunity level of animals, enhance antibody level, enhance TH1 cytokines, promote the production of IgG2a antibodies, and increase T cells proliferation and cytotoxic T lymphocyte (CTL) function.

In another embodiment of the present disclosure, the injection of recombinant human granulocyte macrophage colony stimulating factor (2-30 μg per animal per day) three days before the injection of hepatitis B vaccine, followed by administration of genetically engineered hepatitis B vaccination (1 μg per animal) to chronic hepatitis B transgenic mice model, can effectively break the immune tolerance, produce higher level of anti-hepatitis B antibodies, enhance cellular immunity, and effectively eliminate the hepatocyte of mice expressing hepatitis B antigen. In contrast, the simultaneous injection of recombinant human granulocyte macrophage colony stimulating factor (2-30 μg per animal per day) and genetically engineered hepatitis B vaccine (1 μg per animal) cannot desirably break the immune tolerance for HBV antigen of mice.

In another embodiment of the present disclosure, an antiviral agent (recombinant human interferon type I), a recombinant human granulocyte macrophage colony stimulating factor, and a recombinant hepatitis B vaccine are used in combination. Injecting the antiviral agent 4-0 days before the injection of hepatitis B vaccine and injecting recombinant human granulocyte macrophage colony stimulating factor (2-30 µg per animal per day) three days before the injection of hepatitis B vaccine, followed by administration of genetically engineered hepatitis B vaccination (1 µg per animal) to chronic hepatitis B transgenic mice, can induce higher cellular immune response and enhance the proliferation of T cells.

The present disclosure also provides a vaccine composition for hepatitis B and human immunodeficiency for treating patients infected by hepatitis B and human immunodeficiency virus, which comprises an antiviral agent, an immunomodulatory agent and a hepatitis B vaccine.

DESCRIPTION OF THE EMBODIMENTS

Figure 1:
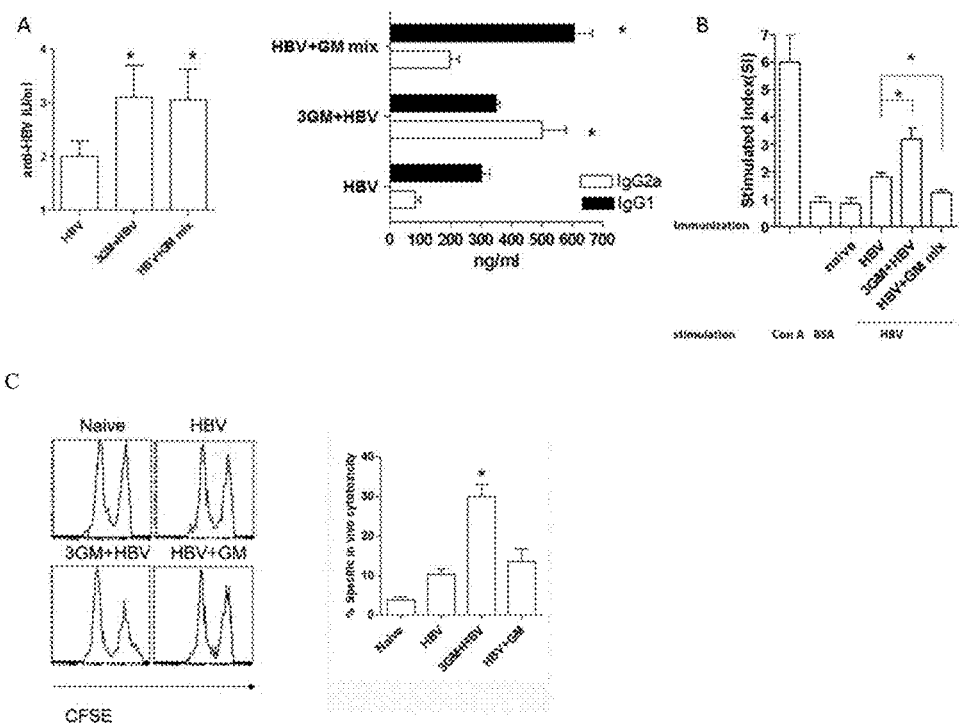
FIG. 1 shows that in embodiment 1, by using quantitative ELISA, A. the measurements of the total IgG and IgG subtype vaccinated by recombinant human granulocyte macrophage colony stimulating factor in combination with hepatitis B vaccine immunity; B. the measurement results of T Lymphocytes amplification with recombinant human granulocyte macrophage colony stimulating factor in combination with hepatitis B vaccine to increase immune response of HBV vaccine in embodiment 1; C. in vivo CTL reaction measured by flow cytometry upon immunization with recombinant human granulocyte macrophage colony stimulating factor in combination with HBV vaccine to increase immune response.

In one aspect, the present disclosure provides methods of overcoming host immune tolerance in a subject having chronic hepatitis B virus (HBV) infection, comprising administering to the subject an immunomodulatory agent and a recombinant HBV vaccine, such that the immune tolerance of the chronic HBV infection in the subject is overcome.

The term "subject" as used herein refers to human and other susceptible animal host for HBV. For example, the subject can be a naïve patients or a HBV patient previously treated with interferon, nucleos(t)ide drug or both.

The term "immune tolerance" as used herein refers to the immune aspect of chronic HBV infection that is clinically manifested as HBsAg positive and no significant immune response to clear the virus.

The term "HBV surface antigen (HBsAg)" refers to an antigen which is found at the virus surface of HBV. HBsAg is usually found in the blood of an infected subject, and if the blood sample of a subject is detected positive for HBV surface antigen, then this normally indicates HBV is present in the subject.

The term "anti-hepatitis B antibody" is an antibody which is capable of binding to or neutralizing HBsAg. Anti-hepatitis B antibody can be protective in the sense that, they can neutralize the HBV antigen and reduce the level of HBV virus. If the level of the anti-hepatitis B antibody is sufficiently high, it may protect the person from hepatitis B infection.

The term "HBsAg seroconversion" refers to the immune status, in which anti-HBsAg antibody appears and develops. After HBsAg seroconversion has occurred, the anti-HBsAg antibody is detectable in the blood.

In certain embodiments, the immune tolerance is overcome such that the HBsAg in serum is substantially reduced or becomes negative in the subject with the appearance of anti-HBsAg antibody in the subject.

In certain embodiments, the immune tolerance of HBV infection can be overcome such that HBsAg disappears over the treatment course and anti-HBsAg appears and its level increases over the time.

Presence of anti-HBsAg antibody typically suggests positive immune response in the subject against the HBsAg. In certain embodiments, the anti-HBsAg antibody in the subject reaches a level sufficient to be protective against future HBV infection.

The term "the immunomodulatory agent" as used herein refers to a drug that has an immunostimulatory effect on the host immune system. Examples of immunomodulatory agent include granulocyte-macrophage colony stimulating factor (GM-CSF), pegylated GM-CSF or derivatives thereof. In certain embodiments, the immunomodulatory agent is recombinant human GM-CSF.

A recombinant HBV vaccine can be a genetically engineered hepatitis B vaccine, such as a subunit protein vaccine of HBV, or a therapeutic HBV vaccine.

In certain embodiments, the immunomodulatory agent is administered to the subject prior to the administration of the HBV vaccine. In certain embodiments, one dose of the immunomodulatory agent is administered 3 days prior to the administration of the recombinant HBV vaccine. In certain embodiments, multiple doses of the immunomodulatory agent are administered in which at least the first dose is administered 3 days prior to the administration of the recombinant HBV vaccine. The immunomodulatory agent can be administered daily for 3 days prior to the administration of the recombinant HBV vaccine.

In certain embodiments, the immunomodulatory agent and the HBV vaccine are administered about 4 to about 12 times for every 12 months at intervals of at least 1 month. In certain embodiments, each of the immunomodulatory agent and the HBV vaccine are administered about 4 to about 12 times for every 12 months at varied intervals of at least 1 month, in particular 1 month to 3 months. The immunomodulatory agent and the HBV vaccine are administered intermittently, i.e., the subject is under temporary but not constant exposure. Without wishing to be bound to theory, such intermittent administration of the immunomodulatory agent and the HBV vaccine can boost the therapeutic effects against HBV infection. Administration of the immunomodulatory agent and the HBV vaccine can be 4-10, 4-9, 4-8, 4-7, 4-6 times for every 12 months at the same or different intervals, such as 1 month, 2 months, 3 months, 4 months, 5 months, 6 months, 7 months, 8 months or 9 months.

In certain embodiments, the immunomodulatory agent and the HBV vaccine are administered 6 times for every 12 months, at varied intervals ranging from 1 month to 3 months.

In certain embodiments, the methods further comprise administering a first antiviral agent.

The term "antiviral agent" as used herein refers to a therapeutic agent having anti-virus effects. An antiviral agent may combat against the virus in various mechanisms, for example, inactivating the replication of the virus, blocking entry of the virus to a host cell, interfering with the packaging or maturation of the virus in the host, or acting against the virus via the host immune system. Antiviral agent for HBV includes, for example, nucleos(t)ide analog, agent that is capable of inhibiting life cycle of HBV, and cytokines. Examples of suitable antiviral agent includes, without limitation, interferon (α-IFN (2a, 2b, 1b) and γ-IFN), peglated interferon (PegIFNα (2a and 2b)) and nucleos(t)ide analogues such as lamivudine (LAM), adefovir dipivoxil (ADV), entecavir (ETV), telbivudine (LdT), tenofovir disoproxil fumarate (TDF), or tenofovir alafenamide fumarate (TAF), and their derivatives. In certain embodiments, the antiviral agent is selected from interferon or nucleos(t)ide analogues, such as IFN-α 3~5 MU, PEG-IFN-α 2a, PEG-IFN-α 2b, lamivudine (LAM), adefovir dipivoxil (ADV), entecavir (ETV), telbivudine (LdT), tenofovir disoproxil fumarate (TDF). An agent which is "capable of inhibiting the life cycle of HBV" as used herein includes, without limitation, HBV capsid inhibitor, HBsAg secretion inhibitor, oligonucleoside targeting HBV mRNAs, and compounds targeting host factors that are critical for HBV replication.

In certain embodiments, the first antiviral agent is interferon, pegylated interferon or an interferon derivative capable of providing sustained release.

In certain embodiments, the first antiviral agent is administered regularly over the course of treatment. The phrase "administered regularly" is intended to mean that the administration is conducted repeatedly and on a regular basis (e.g. daily, twice a day, three times a day, once every two days, once every three days, weekly, and etc.) over the treatment period. A person skilled in the art would understand that the suitable dosing interval of the first antiviral agent can be selected, as long as it can keep the subject under continuous exposure of the first antiviral agent. Dosing intervals may vary for different subjects, or can vary with different antiviral drugs. In certain embodiments, the course of treatment for the first antiviral agent is at least 3, 6, 8, 10, 12 months, or longer. Notably, this regular administration (i.e. continuous exposure) is in contrast to the intermittent administration (i.e. non-continuous exposure) of the immunomodulatory agent and the HBV vaccine.

In certain embodiments, the methods further comprise administering a second antiviral agent which is different from the first antiviral agent. The second antiviral agent can be selected from interferon, nucleos(t)ide analogues, or an agent which is capable of inhibiting the life cycle of HBV.

In certain embodiments, the first antiviral agent is an interferon, pegylated interferon or an interferon derivative and the second antiviral agent is a nucleos(t)ide analog or another agent which is capable of inhibiting the life cycle of HBV (e.g. HBV capsid inhibitor, HBsAg secretion inhibitor, oligonucleoside targeting HBV mRNAs, or a compound targeting host factors that are critical for HBV replication).

In certain embodiments, both the first and the second antiviral agents are administered regularly over the course of the treatment. In certain embodiments, the course of the treatment of the first and/or the second antiviral agents is at least 6 months, at least 8 months, at least 10 months, at least 12 months, at least 14 months, at least 16 months, at least 18 months, or longer.

In certain embodiments, the first antiviral agent is interferon, pegylated interferon or derivative thereof and the second the antiviral agent is a nucleos(t)ide analog or an agent which is capable of inhibiting the life cycle of HBV, and wherein the first and the second antiviral agents are co-administered over the course of the treatment. In certain embodiments, the course of the treatment of the first and/or the second antiviral agents is at least 6 months, at least 8 months, at least 10 months, at least 12 months, at least 14 months, at least 16 months, at least 18 months, or longer.

In certain embodiments, the first antiviral agent is interferon or derivative thereof and the second the antiviral agent is a nucleos(t)ide analog or an agent which is capable of inhibiting the life cycle of HBV, and wherein the first and the second antiviral agents are co-administered for around 3 months before the second antiviral agent is discontinued while the administration of the first antiviral agent continues for the rest of the course of the treatment.

In another aspect, the present disclosure provides methods of treating chronic HBV infection in a subject in need thereof, comprising administering to the subject a first antiviral agent, an immunomodulatory agent and a recombinant hepatitis B vaccine, such that the HBV infection in the subject is treated. HBV carriers who remain HBsAg positive for at least six months may have chronic hepatitis B, which would be reflected by elevated serum alanine aminotransferase (ALT) levels and inflammation of the liver, if they are in the immune clearance phase of chronic infection.

In certain embodiments, the immunomodulatory agent is administered prior to administration of the HBV vaccine.

In certain embodiments, the methods further comprise administering a second antiviral agent which is different from the first antiviral agent.

In another aspect, the present disclosure provides pharmaceutical compositions comprising an HBV vaccine, GM-CSF or pegylated GM-CSF or a derivative thereof, and an antiviral agent such asinterferon. In certain embodiments, the pharmaceutical compositions further comprise an instruction of use in combination with an antiviral agent such as nucleos(t)ide analog or an agent capable of inhibiting HBV life cycle. In certain embodiments, the pharamaceutical composition further comprises an antiviral agent such as nucleos(t)ide analog or an agent capable of inhibiting HBV life cycle. In certain embodiments, the different therapeutic agents in the pharmaceutical composition are packaged in separate containers, to allow separate dosing and administration of the agents. In certain embodiments, the HBV vaccine and GM-CSF or pegylated GM-CSF or a derivative thereof are packaged together in one container and the antiviral agent(s) (for example, interferon, nucleos(t)ide drug or both) are packaged in another container.

BEST MODE TO IMPLEMENT INVENTION

The following embodiments describe the present disclosure in details without limiting the present disclosure. Unless specifically stated, the experimental procedures in the embodiments below are all regular procedures. Unless specifically stated, the percentages in the following embodiments are all weight percentages.

Unless specifically stated, the experimental data in the embodiments of present disclosure is the mean of every mouse in each group.

Embodiment 1

The immune protocol of GM-CSF in combination with recombinant hepatitis B vaccine enhances immune response of C57BL/6 against recombinant hepatitis B subunit vaccine.

Materials and Equipment:

Materials: Genetically engineered (CHO) hepatitis B Vaccine (Recombinant Hepatitis B Vaccine (CHO)), 10 µg/ml, Recombinant Human Granulocyte/Macrophage Colony-Stimulating Factor for Injection, 300 µg/vial, Genetically engineered (CHO) hepatitis B Vaccine stock solution expressed by CHO (HBsAg stock solution), all of which are provided by North China Pharmaceutical Group, Jintan BioTechnology Co., Ltd., Main Kit Equipment: RPMI 1640 medium from WISENT Inc, Fetal bovine serum from Tianjin TBD Science, Mouse anti rabbit IgG from Sigma, HRP labelled anti mouse IgG IgG1, IgG2a from Southern Biotechnology Assosiates, Brimingham, Ala., USA. Red blood cell lysis buffer: 8.29 g $NH_4Cl$, 1 g $KHCO_3$, 37.2 mg $Na_2EDTA$ were dissolved in deionized water to get a total volume of 800 ml and the pH value was adjusted to 7.2-7.4, then deionized water was added to get a total volume of 1000 ml. The solution was filtrated and sterilized, and stored at room temperature. Fiber glass column: fiber glass was filled into disposable 1ml syringe to get fiber glass column used for T cell isolation. MTT: The purchased MTT powder was dissolved in PBS (the concentration is 5 mg/ml i.e. 0.5% MTT) then filtered and sterilized, and then stored at −20° C. in dark. ConA: ConA powder was dissolved in serum free RPMI1640 medium to a concentration of 60 µg/ml. Fluorescently labeled monoclonal antibodies: the commonly used ones include FITC, PE, and APC labeled monoclonal antibodies purchased from BD, eBioscience, and BioLegend. Blocking antibody: Anti Fc receptor antibody, the Fc receptor is usually expressed on the surface of immune cells, and can bind the Fc fragment of the antibody. The function of blocking antibody is to block the non-specific result generated by the bonding of Fc fragment of the fluorescently labeled monoclonal antibodies to the immune cell surface Fc receptor. Fix buffer: 4% paraformaldehyde in PBS; Permeabilization buffer: 1% saponin; in vitro stimulating CTL polypeptide of Hepatitis B surface antigen was synthesized by GL Biochem (Shanghai) Ltd.; Hepatitis B surface antibody diagnostic kit and standard were purchased from Beijing Kinghawk Pharmaceutical Co., LTD. Centrifuge: product from Eppendorf; Flow cytometer: FACScalibur manufactured by BD Bioscience.

Animal and immunization: Female 6-8-week old SPF C57BL/6 mice with a weight of 16-18 g were purchased from Lab Animal Research Institute of China Academy of Medical Science. The animals were divided into 4 groups with 6 mice per group as listed in the table below. The vaccine or GM-CSF dissolved in saline was injected 100 ul per animal via cervix subcutaneous injection, and the animals were boosted once 14 days after the first immunization.

| Experimental groups | | |
| --- | --- | --- |
| Groups | Vaccine | GM-CSF |
| 1. Naive | 0 g | |
| 2. HBV | 1 µg HBV vaccine (0 day) | 0 µg |
| 3. 3GM-CSF + HBV | 1 µg HBV vaccine (0 day) | 10 µg GM-CSF (−3, −2, −1 day) |
| 4. HBV + GM-CSF | 1 µg HBV vaccine (0 day) | 30 µg GM-CSF (0 day) |

Serum collection from mouse: 200-300 µL of mouse ocular fundus artery blood samples were collected with sterilized glass capillary into sterile microcentrifuge tube. The blood sample stands at room temperature for 30 minutes and at 4° C. for 2 hours, and centrifuged at 5000 rpm for 10 minutes to collect the supernatant, which was stored at −20° C. for further use.

Total IgG Titer in the Serum Measured by ELISA:

(1) Antigen coating: 1 ug/ml antigen was coated on 96-wells microplate with 100 ul/well, and was placed at 4° C. overnight;

(2) Blocking: The plate was washed by PBST (0.05% Tween20 dissolved in PBS) for 3 times, with each time lasting for 5 minutes. Then 5% skimmed milk was used to block the plate with 100 µl/well at 37° C. for 1 h;

(3) Serum addition: The plate was washed by PBST for 3 times, with each time lasting for 5 minutes. 2-folds serial diluted mouse serum were added with 100 µl/well using naive mouse serum as control. The plate was then incubated at 37° C. for 1 hour;

(4) Secondary antibody addition: The plate was washed by PBST for 3 times, with each time lasting for 5 minutes. HRP labelled goat anti mouse IgG (1:1000) was added to each well with 100 µl/well. The plate was then incubated at 37° C. for 1 hour;

(5) Color development: The plate was washed by PBST for 3 times, with each time lasting for 5 minutes. Substrate TMB was added with 100 µl/well to develop color. The plate was then placed at 37° C. in dark for 15 minutes to develop color;

(6) Reaction stopping: 0.2M $H_2SO_4$ was added to stop the color development with 50 µl/well;

(7) Reading out: Optical density was measured at OD 450 nm/620 nm. It is considered as positive when the OD value of the sample well is 2 times of the control well.

The Concentration of IgG1 and IgG2a in the Serum Measured by ELISA:

(1) Antigen coating: Rabbit IgG (2 µg/ml) and VP1 antigen (1 µg/ml) were coated on 96-wells microplate with 100 µl/well, the plate was then placed at 4° C. overnight;

(2) Blocking: The plate was washed by PBST (0.05% Tween 20 dissolved in PBS) for 3 times, with each time lasting for 5 minutes. 3% BSA solution was added with 100 µl/well to block the plate at 37° C. for 1 h;

(3) Serum addition: The plate was washed by PBST for 3 times, with each time lasting for 5 minutes. Mouse anti rabbit IgG was diluted by 10 continuous 2-folds serial dilutions from 20 ng/ml and mouse serum was diluted by 1:100, both were then added to wells in triplicate with 100 µl/well. The plate was then incubated at 37° C. for 1 hour;

(4) Secondary antibody addition: The plate was washed by PBST for 3 times, with each time lasting for 5 minutes. HRP labeled goat anti mouse IgG1 and IgG2a (1:1000) were added to well with 100 µl/well. The plate was then incubated at 37° C. for 1 hour;

(5) Color development: The plate was washed by PBST for 3 times, with each time lasting for 5 minutes. Substrate TMB was added with 100 µl/well to develop color. The plate was then placed at 37° C. in dark for 15 minutes to develop color;

(6) Reaction stopping: 0.2M $H_2SO_4$ was added to stop the color development with 50 µl/well;

(7) Reading out: Optical density was measured at OD 450 nm/620 nm. It is considered as positive when the OD value of the sample well is 2 times of the control well;

(8) Standard curve was plotted and the amount of antibody was calculated.

Procedure of T Cells Proliferation:

T Cells in Vitro Proliferation Activity was Measured by MTT.

(1) All materials used in the experiments need to be sterilized in advance.

(2) The mice were sacrificed by disjoint and were soaked in 70% ethanol for 15 minutes.

(3) The spleens of the mice were taken out under aseptic condition on a ultra-clean working table that had been sterilized by UV light for 20 minutes in advance, and were put into cell-culture dish containing 2 ml of RPMI1640 medium.

(4) Copper screen was burned and cooled then put into the plate. The spleens were smashed with sterilized syringe and prepared as cell suspension, which was then filtered into 13 ml cell centrifuge tube.

(5) The centrifuge tubes were sealed with membrane and centrifuged at 2000 rpm for 10 minutes.

(6) The supernatant was discarded, then 2-3 ml of red blood cell lysis buffer was added into the tubes to suspend the cells. After 2 minutes of lysis, equal volume of RPMI1640 medium (or fetal bovine serum) was added to stop the reaction. The tubes were sealed with membrane and centrifuged at 2000 rpm for 10 minutes.

(7) The supernatant was discarded, then 3-4 ml of RPMI1640 medium (containing 2% fetal bovine serum) was added into the tubes to suspend the cells.

(8) The cell suspension was slowly filtered with glass fiber at 37° C. to thoroughly combine the cells and the glass fiber to remove the B cells.

(9) The cell density was counted using blood cell counting chamber.

(10) The cell density was adjusted to $3\sim4\times10^6$/ml with RPMI1640 medium (containing 2% fetal bovine serum).

(11) The cell suspension with adjusted concentration was added to 96-well plate with 100 µl per well.

(12) The antigen was sterilized and diluted to a certain concentration. Then 20 µl of stimulus was added to each well (final concentration of the stimulus was: ConA 10 µg/ml, 5 µg/ml, BSA/OVA 2 µg/ml. The stimulus can be diluted and added according to different concentrations). The control cell only wells without stimulus and medium only wells were set up.

(13) The cells were put into the incubator and incubated at 37° C. under 5% $CO_2$ for 48~72 hours. Then MTT method was used for color development (20 µl of MTT was added into each well and the data was read out after 3-4 hours) experimental sample OD−medium OD.

(14) The supernatant was discarded and 150 µl of dimethyl sulfoxide was added to each well. The plate was then placed on the shaking bed to be shaken at low speed for 10 minutes to fully dissolve the crystals. OD value at 490 nm was measured by microplate reader (Magellan, Tecan Austria GmbH).

(15) Calculating results: SI=(OD of stimulated wells−OD of medium only)/(OD of unstimulated wells−OD of medium only).

Procedure for Surface and Intracellular Staining:

(1) Pure T cells were isolated from the mice to 10% medium and was diluted to $1\times10^7$ cells/ml.

(2) 100 ul of the cell and short peptide having a final concentration of 10 µg/ml were added to 96 cell plate. CD28 monoantibody having a final concentration of 10 µg/ml can also be added for costimulatory signal. After thorough mixing, the mixture was incubated at 37° C. under 5% $CO_2$.

(3) After stimulation for 4-6 hours, monensin protein inhibitor was added 2 µl/well into each well.

(4) After monensin inhibition for 2 hours, the cells were centrifuged with 2 ml of PBS at 2000 rpm for 5 minutes, and re-suspended in 100-200 µl of PBS. Purified FcII/III receptor antibody (CD16/32) was added according to the usage of 1 µg/106 cells to eliminate non-specific bind staining, incubated in ice bath for 15-20 minutes and centrifuged with 2 ml PBS at 2000 rpm for 5 minutes.

(5) The cells were re-suspended in 200 µl of PBS solution with 4% paraformaldehyde and incubated at room temperature for 10-15 minutes, then centrifuged with 2 ml of PBS at 2000 rpm for 5 minutes.

(6) The cells were re-suspended in 200 µl of PBS solution with 0.1% saponin and incubated at 4° C. for 10 minutes, then centrifuged with 2 ml of PBS at 2000 rpm for 5 minutes.

(7) Surface molecules and intracellular cytokine were stained.

Two kinds of florescent antibodies were added to the cells simultaneously according to the description, incubated in ice bath for 20-30 minutes and centrifuged with 2 ml of PBS at 2000 rpm for 5 minutes. The cells were re-suspended in 300 µl of PBS and the cell suspension was filtered through copper screen into specialized FACS tube for measurement and analysis by instruments.

Procedures for in vivo CTL:

Splenocytes were obtained by breaking and isolating red cells of naive mice.

(1) The splenocytes were evenly divided into two culture dishes. In one dish 50 g of T cell epitope peptide fragments were incubated, while in the other no peptide fragments were incubated. With a volume of 1-2 ml in each dish, the dishes were incubated at 37° C. under 5% $CO_2$ for 4 hours (the number of target cells can be increased according to the number of experimental groups in this step).

(2) The cells were transferred into 15 ml Falcon tubes and centrifuged at 3000 rpm for 5 minutes.

(3) The target cells without incubating small peptides were stained with a low concentration of CFSE (0.5 μM), while the target cells incubating small peptides were stained with a high concentration of CFSE (5 μM), both being gently shaken for 15 minutes at 37° C. in dark.

(4) Equal volume of fetal bovine serum were added to stop the reaction after staining. The supernatant was discarded after the solution was centrifuged at 3000 rpm for 5 minutes. The cells were then washed with 10 ml PBS three times.

(5) Equal volume of target cells being stained with low concentration and high concentration were mixed together and were injected back into experimental mice $2 \times 10^7$ cells per mouse through tail vein to carry out cytotoxic activity of cell in vivo.

(6) The mice were sacrificed 4 hours after the injection. Splenocytes were isolated in dark.

(7) The sample was filtered by copper screen and transferred into specialized FACS tube for measurement and analysis by instruments.

The results were analyzed by t-test for statistical analysis. $p<0.05$ indicates significant difference and $p<0.01$ indicates very significant difference.

Figure 2:
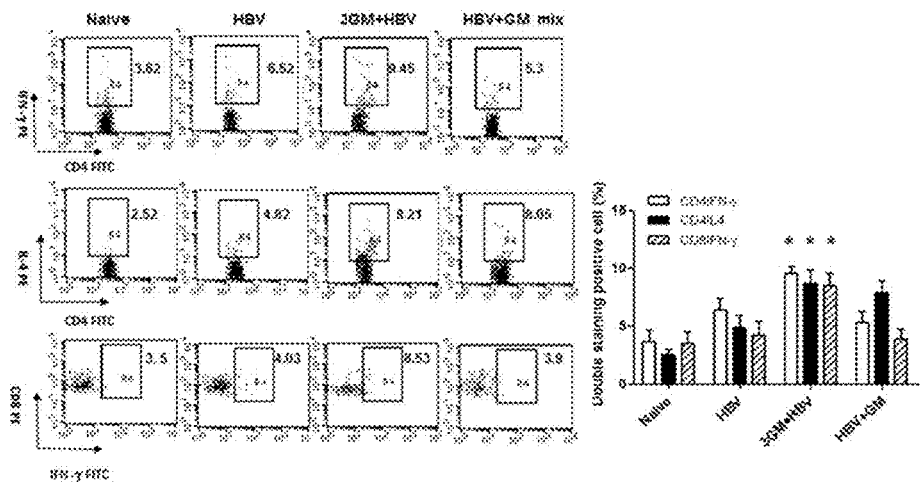
FIG. 2 shows the IFN-γ, IL-4 expression in CD4 T cells and IFN-γ expression in CD8 T cells measured by flow cytometry upon immunization with recombinant human granulocyte macrophage colony stimulating factor in combination with HBV vaccine to increase immune response of HBV vaccine in embodiment 1.

Experimental Results:

1. In order to test whether GM-CSF can affect the humoral response of HBV vaccine, GM-CSF was injected in advance or simultaneously with HBV vaccine. Total IgG against HBsAg in the serum was measured 7 days after the boost immunization. Compared with the group that was injected with HBV vaccine only, the IgG level in the group that was injected with GM-CSF was significantly increased (FIG. 1-A). The IgG2a level was significantly enhanced in the group that was injected with GM-CSF 3 days before the immunization ($p<0.05$); on the contrary, the IgG1 level was significantly enhanced in the group that was injected with GM-CSF and HBV simultaneously (FIG. 2-1B). Results indicate that pre-treatment with GM-CSF can enhance Th1 response, while the simultaneous injection of GM-CSF and vaccine can enhance Th2 response.

2. The effect of GM-CSF injected at different times on T cell level of Hepatitis B vaccine.

To further observe whether GM-CSF can affect T cell response, mouse splenocytes were taken out aseptically one week after the boost immunization. The T cell proliferation was stimulated with rHBsAg antigen, using BSA as non-specific antigen control, ConA as positive control, and medium as negative control. Results showed that T cell proliferation was significantly increased in the group with GM-CSF pre-injection. However, the level of T cell proliferation was low in the group that was injected with GM-CSF and HBV vaccine simultaneously (FIG. 1-B), which indicated that GM-CSF pre-treatment could promote antigen specific T cell response.

3. The effect of GM-CSF injected at different times on in vivo CTL level of Hepatitis B vaccine.

To understand the effect of GM-CSF injected at different times on CTL response, CTL response was measured by flow cytometry 7 days after the second immunization. As indicated in FIG. 1-C, the specific kill rate of target cells is 30.01% in the group with GM-CSF pre-treatment, which is much higher than the group with immune nucleic acid vaccine alone having a specific kill rate of 10.26%. Whereas the specific kill rate is 13.6% in the group that was injected with GM-CSF and HBV simultaneously. The results indicated that GM-CSF pre-treatment could enhance the level of in vivo CTL response, whereas there was no obvious change in the group that was injected with GM-CSF and HBV simultaneously.

4. The effect of GM-CSF injected at different times on the level of in vivo cytokine of Hepatitis B vaccine Cytokine can regulate cell differentiation and proliferation, and induce cells to function accordingly, so it plays an important role in regulating immune response. In this experiment, the expression level of antigen specific IL-4 and IFN-γ in CD4+ T cells and antigen specific IFN-γ in CD8+ T cells were measured by intracellular cytokine staining. As indicated in FIG. 2, the level of IL-4, IFN-γ (in CD4+ cells) and IFN-γ (in CD8+ cells) in GM-CSF pre-treated group was significantly improved compared to HBV injected alone group. Whereas in the group that was injected with GM-CSF and HBV vaccine simultaneously, there was no increase in the expression level of IFN-γ, with only IL-4 expression level being increased compared to control group. The results indicated that GM-CSF pre-treated group can enhance cytokine expression of both Th1 and Th2, while the simultaneous injection of GM-CSF and HBV vaccine could only induce the expression of Th2.

Embodiment 2

GM-CSF in combination with recombinant Hepatitis B vaccine breaks immune tolerance and induce humoral immune response against Hepatitis B surface antigen and HBsAg positive hepatocytes in HBsAg transgenic mouse.

Materials and Equipment:

HBsAg transgenic mice (C57BL/6J-Tg(A1b1HBV) 44Bri/Jf4J) were purchased from Shanghai Public Health Clinical Center, which is the affiliated organization of Fudan University. "Hepatitis B surface antigen enzyme-linked immunosorbent assay diagnostic kit" and Hepatitis B surface antigen standard were purchased from Beijing Kinghawk Pharmaceutical Co., LTD. Other experimental materials, main reagents, and equipments are the same as listed in embodiment 1.

Experimental Method:

Animal Groups and Immunization:

35 HBsAg transgenic mice (C57BL/6J-Tg(A1b1HBV) 44Bri/Jf4J) (with original HBsAg concentration at 5000-10000 pg/ml) were divided into 5 groups randomly with 7 mice per group as listed in the "Experimental Immune Groups" table below. The vaccine or GM-CSF in each group dissolved in saline was injected 100 μl per animal via cervix subcutaneous injection. The mice in each group were immunized four times with 14 days interval between the first, the second, and the third immunization and 8 weeks interval between the third and the fourth immunization. Orbital blood of the mice was collected every 2 weeks and the concentration of hepatitis B surface antigen and hepatitis B surface antigen antibody in the serum of transgenic mice were measured by ELISA.

| Experimental Immune Groups | | |
|---|---|---|
| Groups | Vaccine | GM-CSF |
| Naive | 0 g | |
| HBV | 1 µg HBV vaccine (0 day) | 0 µg |
| 3GM-CSF + HBV | 1 µg HBV vaccine (0 day) | 10 µg GM-CSF (−3, −2, −1 day) |
| 30GM-CSF + HBV | 1 µg HBV vaccine (0 day) | 30 µg GM-CSF (0 day) |
| 10GM-CSF + HBV | 1 µg HBV vaccine (0 day) | 10 µg GM-CSF (0 day) |

The HBVs Antigen Level of HBVs Antigen Transgenic Mice was Measured by Hepatitis B Surface Antigen Diagnostic Kit:

1. Dilution of antigen standard (2 mg/ml): 2-folds serial dilution was performed from 10^6. 2 ul of AG was diluted with PBS to 20 ul (10×), from which 10 ul was drawn and diluted with PBS to 1 ml (100×2 ug), from which 500 ul was drawn and diluted with PBS to 1 ml (2×1 ug). 2-folds serial dilution was continued for 14 times. An 8-points standard curve was drawn using the last 7 dilutions and PBS group.

2. Dilution of serum: 10×, 50×, and 100× dilution of serum with triplicate pores for each sample was performed.

3. According to the experimental requirements, certain amounts of reaction stripes was selected. 75 µl of the diluted sample was added into each well, with each of negative control, positive control, and blank in one individual well.

4. The plate was sealed and incubated at 37° C. for 60 minutes.

5. The plate was taken out and the seal was removed. 50 µl of enzyme-substrate complex was added to each well and was shaken for 10 seconds. The plate was sealed and incubated at 37° C. for 30 minutes.

6. The plate was taken out followed by removal of the seal, and was washed for 5 times and dried out.

7. Color developing solution was prepared with an A and B ratio of 1:1. 100 µl of thoroughly mixed color developing solution was added to each wells, shaken for 10 seconds, and incubated at 37° C. for 30 minutes.

8. 50 µl of stop solution was added into each well and was shaken to mix well. The results were measured by microplate reader at a wavelength of 450 nm and a reference wavelength of 630 nm.

The HBVs Antibody Level of HBVs Antigen Transgenic Mice was Measured by Hepatitis B Surface Antibody Diagnostic Kit:

1. Dilution of HBsAb standard (40 mIU): 2-folds serials dilution was performed from original standard solution for 7 times, based on which and PBS group an 8-points standard curve was drawn.

2. Dilution of serum: 10×, 50×, and 100× dilutions of serum with triplicate pores for each sample were performed.

3. According to the experimental requirements, certain amounts of reaction stripes were selected. 50 µl of the diluted sample was added into each corresponding well, with each of negative control, positive control, and blank being in one individual well. 50 µl of enzyme-substrate complex was added into each well and was shaken for 10 seconds. Then the plate was sealed with sealing paper and incubated at 37° C. for 30 minutes.

4. The plate was taken out followed by removal of the seal, and was washed for 5 times and dried out.

5. Color developing solution was prepared with an A and B ratio of 1:1. 100 µl of thoroughly mixed color developing solution was added to each wells, shaken for 10 seconds, and incubated at 37° C. for 30 minutes.

6. 50 µl of stop solution was added into each well and was shaken to mix well. The results were measured by microplate reader at a wavelength of 450 nm and a reference wavelength of 630 nm The result was analyzed by t-test for statistical analysis. $p<0.05$ indicates significant difference and $p<0.01$ indicates very significant difference.

Figure 3:
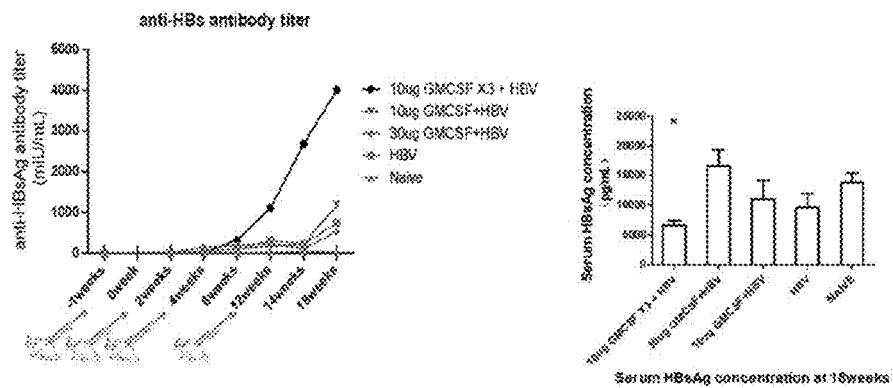
FIG. 3 shows the change in hepatitis B surface antigen antibody of hepatitis B surface antigen transgenic mice, whose immune tolerance has been broken by recombinant human granulocyte macrophage colony stimulating factor in combination with hepatitis vaccine, and the decrease of hepatitis B surface antigen in transgenic mice in embodiment 2.

Experimental Results:

1. In order to test whether the strategy of GM-CSF in combination with recombinant Hepatitis B vaccine can break the immune tolerance and induce the humoral immune response of Hepatitis B surface antigen in HBsAg transgenic mouse, GM-CSF was injected before or with HBV vaccine. The concentration of HBsAg and total IgG against HBsAg were measured every two weeks. Compared with the group that was injected with HBV alone, the total level of IgG was significantly increased in the group with 3GM-CSF+HBV (FIG. 3). The level of Hepatitis B surface antigen was significantly decreased ($p<0.05$) six weeks after the fourth immunization in the group injected with GM-CSF three days in advance (3GM-CSF+HBV). The results indicated that 3GM-CSF+HBV group (i.e. the group that was injected with GM-CSF 3 days in advance) could break the immune tolerance of transgenic mice and induce the humoral immune response of Hepatitis B surface antigen in HBsAg transgenic mouse to further keep the hepatitis B virus surface antigen at a low level. While there was no significant increase in antibody against Hepatitis B surface antigen in the groups that was injected with HBV vaccine alone and injected with GM-CSF and HBV simultaneously.

Embodiment 3

The strategy of GM-CSF in combination with recombinant Hepatitis B vaccine breaks immune tolerance of HBsAg transgenic mouse, induces the immune response against Hepatitis B virus surface antigen positive hepatocytes, and clears the Hepatitis B virus surface antigen in liver.

Materials and Equipment:

HBsAg transgenic mice (C57BL/6J-Tg(A1b1HBV) 44Bri/Jf4J) were purchased from Shanghai Public Health Clinical Center, which is the affiliated organization of Fudan University. The first and second immunohistochemistry antibodies against Hepatitis B virus surface S antigen are purchased from Shanghai Long Island Biotec. Co., Ltd. Other experimental materials, main reagents, and equipments are the same as listed in embodiment 1.

Animal Groups and Immunization:

35 HBsAg transgenic mice (C57BL/6J-Tg(A1b1HBV) 44Bri/Jf4J) (with original HBsAg concentration at 5000-10000 pg/ml) were divided into 5 groups randomly with 5 mice per group as listed in the table below. The vaccine or GM-CSF in each group dissolved in saline was injected 100 µl per animal via cervix subcutaneous injection. The mice in each group were immunized three times each with 14 days interval. Delayed-Type Hypersensitivity (DTH) was performed 12 days after the third immunization. The mice were sacrificed 15 days after the third immunization and the splenocytes were isolated and liver immunohistochemistry was performed.

| Experimental immune groups design | | |
|---|---|---|
| Groups | Vaccine | GM-CSF |
| Naive | 0 μg | |
| HBV | 1 μg HBV vaccine (0 day) | 0 μg |
| GM-CSF | 0 μg | 10 μg GM-CSF (0 day) |
| 3xGM-CSF + HBV | 1 μg HBV vaccine (0 day) | 10 μg GM-CSF (−3, −2, −1 day) |
| 30GM-CSF + HBV | 1 μg HBV vaccine (0 day) | 30 μg GM-CSF (0 day) |

Delayed-Type Hypersensitivity (DTH) Detection:

12 days after the third immunization, for all mice in both the experimental group and the control group, rHBsAg antigen (2 μg) was injected into the dorsal right footpad and saline was injected into the dorsal left footpad. Footpad thickness was measured by vernier calipers 24, 48 and 72 hours after the injection, and was calculated by the equation as below: swelling thickness (mm)=the thickness of right footpad−the thickness of left footpad. The value of swelling thickness reflects the level of Delayed-Type Hypersensitivity (DTH).

The measurement of the level of cytokine expression by Flow cytometry is the same as listed in embodiment 1.

Histology Measurement:

HBsAg transgenic mice were anesthetized 14 days after the last immunization to have the liver issue fixed, embedded, and sliced. H&E staining and immunohistochemistry experiments were performed individually. The antibody used in immunohistochemistry was anti-HBsAg antibody.

Preparation of the Tissue Slides:

(1) Sampling: Transgenic mice was sacrificed by anesthesia and the liver tissue of the mice was taken out;

(2) Fixation: The liver tissue were placed into Bouin solution immediately;

(3) Dehydration and transparency: The tissue was dehydrated using alcohol at low to high concentration;

(4) Paraffin immersing: The tissue was immersed into paraffin I at 56° C.-58° C. for about 1 hour, paraffin II at 56° C.-58° C. for about 1 hour, and paraffin III at 56° C.-58° C. for about 1-2 hours;

(5) Embedding: The tissue blocks were put into pre-folded small paper boxes, with paraffin added in;

(6) Trimming of the paraffin blocks: The paraffin blocks were trimmed into trapezoid to facilitate the formation of paraffin tape;

(7) Section: The thickness of the section is about 8-10 μm;

(8) Mounting: The paraffin tape was floated in a water bath stretching machine with a temperature adjusted to 38° C. Once the paraffin tape was extended, it was collected using a glass slide and was observed under a microscope to ascertain and select the tissue morphology;

(9) Toasting: The mounted sections were put into an oven at a temperature greater than 41° C. and not greater than 50° C. for at least 4 hours to attach the tissue to the slide firmly.

Immunohistochemistry of the Tissue Section:

(1) The sections having good histomorphology were rehydrated using ethanol in gradient, and then soaked in PBS (0.01 M; pH 7.4) for three times with each time lasting for 5 minutes.

(2) Antigen unmasking: The sections were put into container with citric acid buffer and were heated in microwave at high temperature for 5 min×3. If there was a loss of liquid, hot distilled water needed to be added.

(3) The sections were blocked with serum used for blocking or BSA in an incubator at 37° C. for at least 1 hour.

(4) The serum was drained without washing. The first antibody diluted in suitable ratio was used to cover the sections, and then blocked at 27° C. for 1 hour or at 4° C. overnight.

(5) The sections were washed with PBS for three times with each time lasting for 5 minutes.

(6) Biotin labelled secondary antibody diluted in suitable ratio (diluted using 1% BSA-PBS) was dropped on the sections, and then incubated at 27° C. for 30-40 minutes.

(7) The sections were washed with PBS for three times with each time lasting for 5 minutes.

(8) The third antibody diluted in suitable ratio was dropped on the sections, and then then incubated at 27° C. for 30 minutes.

(9) Color was developed using alkaline phosphatase in dark. The positive AP color developing result should be specific red color.

(10) The sections were rinsed with tap water.

(11) Re-staining: The procedure of staining was to stain for 1-3 minutes using Harris hematoxylin and to differentiate for 1 minute using weak acid solution (1-2 drops of 1M hydrochloric acid can be added into distilled water), followed by rinse for three minutes using tap water. Eosin-phloxine staining was directly performed for 1 minute.

(12) The sections were dehydrated and dried in the fume hood for observation of the histomorphology;

The sections were stored in the storage box, and were photographed and observed for suitable scale, color adjustment, and selection of suitable positive results.

The results were analyzed by t-test for statistical analysis. $p<0.05$ indicates significant difference while $p<0.01$ indicates very significant difference.

Figure 4:
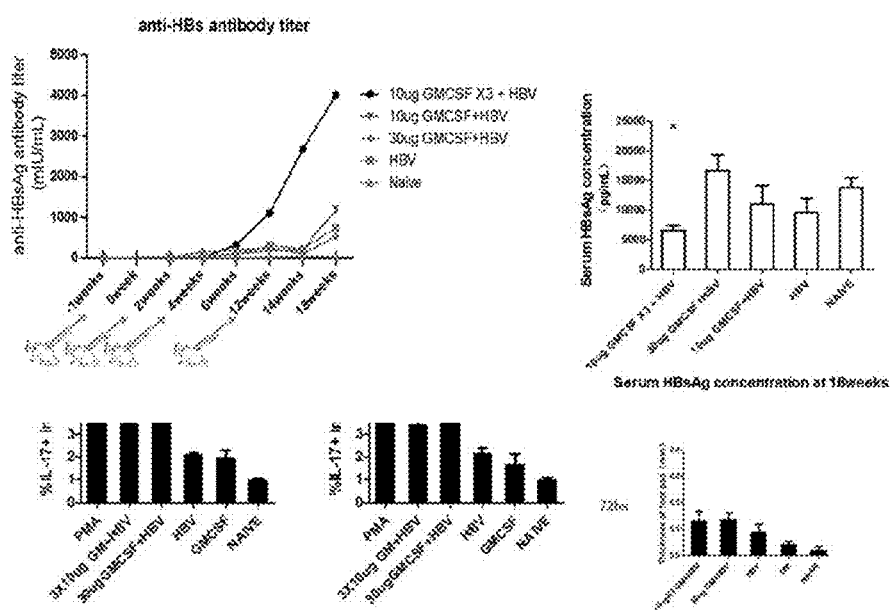
FIG. 4 shows A. the IL-10 and IFN-γ expression in CD4 and CD8 T cells measured by flow cytometry after the immune tolerance of hepatitis B surface antigen transgenic mice has been broken by recombinant human granulocyte macrophage colony stimulating factor in combination with hepatitis B vaccine in embodiment 2; B. the measurements of DTH after vaccination by recombinant human granulocyte macrophage colony stimulating factor in combination with hepatitis B vaccine to increase immune response of hepatitis B vaccine in embodiment 2.

Experimental Results:

1. GM-CSF in combination with recombinant Hepatitis B vaccine immunization enhanced Delayed-Type Hypersensitivity level of hepatitis B virus surface antigen transgenic mouse: Delayed-Type Hypersensitivity is a type of immune response mediated by T cells. In order to evaluate whether the immune strategy of GM-CSF in combination with recombinant Hepatitis B vaccine can induce strong in vivo cellular immunity level, the Delayed-Type Hypersensitivity level was used as the in vivo indicator. Immunization was performed according to experimental groups. 12 days after HBsAg transgenic mice (C57BL/6J-Tg(A1b1HBV)44Bri/Jf4J) were immunized for the third time, for all mice from experimental groups and control groups, rHBsAg was injected into the dorsal right footpad and saline was injected into the dorsal left footpad. The right and left footpad thickness was measured 24, 48, and 72 hours after injection. It is shown in FIG. 4-B that the group immunized with hepatitis B vaccine only has a higher DTH level than the control group, whereas the DTH level in the groups with the immune strategy of GM-CSF in combination with recombinant hepatitis B vaccine (3*GM-CSF+HBV and 30 μg GM-CSF+HBV groups) is significantly increased compared with the group that was injected with hepatitis B vaccine alone, indicating that the groups with the immune strategy of GM-CSF in combination with recombinant hepatitis B vaccine (3*GM-CSF+HBV and 30 μg GM-CSF+HBV groups) induced strong cellular immune response in vivo.

2. The immune strategy of GM-CSF in combination with recombinant hepatitis B vaccine enhanced DTH level mediated by CD8+ T cells, and may improve the activity of CD8+ T killer cells. The CD8+ T cells that secrete IFN-γ (Tc1) and the CD8+ T cells that secrete IL-17 (Tc17) are two groups of vital CD8+ T killer cells. The expression of IFN-γ and IL-17 in CD8+ T cells of immunized mice were further detected in this experiment. The spleens of the immunized mice were taken out under aseptic condition after 15 days of the third immunization, and were used to prepare unicellular suspension for the incubation of CD8+ T cell epitope polypeptide of hepatitis B virus surface antigen in vitro. After six hours of incubation, the intracellular cytokine was stained, and analyzed by flow cytometry for the change of the subtype cell populations. As showed in FIG. 4-A, the immune strategy of GM-CSF in combination with recombinant hepatitis B vaccine can enhance the level of IFN-γ and IL-17 that were secreted by CD4+ and CD8+ T cells, while the immune strategy of 3*GM-CSF+HBV is more likely to induce the immune response of Th1 and Tc1, and the immune strategy of 30 µg GM-CSF in combination with HBV is more likely to induce immune response of Th17, Tc17.

Figure 5:
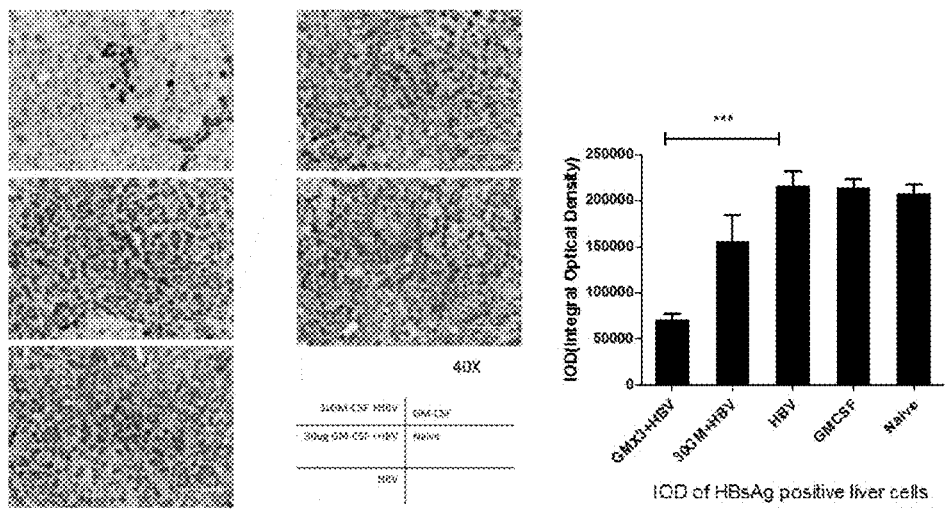
FIG. 5 shows histochemistry staining of hepatitis B surface antigen on the liver surface in hepatitis B antigen transgenic mice after the immune tolerance of hepatitis B surface antigen transgenic mice has been broken by recombinant human granulocyte macrophage colony stimulating factor in combination with hepatitis B vaccine in embodiment 2, and the average optical density of the hepatitis B antigen expression in hepatocyte of treated transgenic mice.

3. HBsAg transgenic mice were anesthetized 14 days after the last immunization. The liver issue was fixed, embedded, and sliced. H&E staining and Immunohistochemistry experiments were performed individually. FIG. 5 is the immunohistochemistry photo and statistic photo of optical density for hepatitis B virus surface antigen of the hepatitis B virus surface antigen of the liver of transgenic mice. It is shown that the hepatitis B virus surface antigen in the liver of transgenic mice is significantly cleared under the immune strategy of 3*GM-CSF+HBV. Although there is some decrease of the hepatitis B virus surface antigen in the liver in the group using immune strategy of 30 µg GM-CSF in combination with HBV, the clearing effect is not as significant as the group using immune strategy of 3*GM-CSF+HBV. Results showed that the GM-CSF+HBV immunization broke the immune tolerance of the hepatitis B virus surface antigen transgenic mice, induced strong humoral and cellular immune response in hepatitis B virus surface antigen transgenic mice, and effectively cleared hepatitis B virus surface antigen in serum and liver.

Embodiment 4

The effect of type I interferon injected at different times on the immune strategy of GM-CSF in combination with recombinant hepatitis B vaccine Materials and Equipment:

Recombinant human interferon α 1b (50 µg/ml/vial) was purchased from Beijing Tri-Prime Genetic Engineering Co., Ltd. Other experimental materials, main reagents, and equipments are the same as listed in embodiment 1, 2 and 3.

Experimental Animals and Immunization:

Female 6- to 8-week old SPF C57BL/6 mice with a weight of 16-18 g were purchased from Lab Animal Research Institute of China Academy of Medical Science. The animals were divided into 8 groups with 6 mice per group as listed in table 1. The vaccine or GM-CSF in each group dissolved into saline was vaccinated into the animals with 100 ul per animal via cervix subcutaneous injection. The animals were boosted 14 days after the first immunization. $5*10^4$ U interferon was injected to each animal via cervix subcutaneous injection according to the experimental groups.

TABLE 1

Experimental immune groups

| GROUPS | | GMCSF | IFN-a | HBV vaccine | Mouse |
|---|---|---|---|---|---|
| A | NAIVE | — | — | — | 6 |
| B | HBV | — | — | 1ug | 6 |
| C | (arrows) | 10ug/d X3d | $5*10^4$U | 1ug | 6 |
| D | (arrows) | 30ug/d X1d | $5*10^4$U | 1ug | 6 |
| E | (arrows) | — | $5*10^4$U | 1ug | 6 |
| F | (arrows) | 10ug/d X3d | — | 1ug | 6 |
| G | (arrows) | 30ugX1d | — | 1ug | 6 |
| H | (arrows) | 30ug/d X1d | $5*10^4$U | 1ug | 6 |

↑ IFN-a    ↑ GMCSF    ↑ HBV vaccine

The detection of hepatitis B surface antigen by ELISA, the experiments of T cells proliferation, and the detecting method of cytokine of T cells using flow cytometry can all refer to embodiment 1.

T Cells Proliferation Measured by CFSE Method:

1. The mice were sacrificed conventionally, and were soaked in 75% ethanol for 5-10 minutes.
2. The spleens of the mice were taken out, added with 600 ul PBS or RPMI1640 medium and smashed. The large tissues were filtered by copper screen. The supernatant was discarded after centrifugation at 1500 rpm for 3 minutes.
3. Red cells lysis by RBC: 700 ul RBC lysis cell was added into each tube for 2 minutes (the lysis duration should be controlled strictly). 700 ul of FBS was added to stop the lysis. Then the tubes were centrifuged at 1500 rpm for 3 minutes, and the supernatant was discarded. The cells were re-suspended with 1 ml 1640 or PBS.
4. Count the cells, and adjust the cell concentration to $1\times10^7$/ml.
5. 500 ul PBS solution containing 1 ul of 1 mM CFSE was added into 500 ul of re-suspended cells, mixed thoroughly and inverted for 10 times, followed by staining in dark for 10 minutes at 37° C. in a shaker. 500 ul of FBS was added to stop staining, followed by centrifugation at 2000 rpm for 3 minutes. RPMI1640 medium containing 15% FBS serum or PBS was added to wash for 3 times.
6. Count the cell, and adjust the cell concentration to $1\times10^7$/ml with complete medium. Then the cells were mixed thoroughly.
7. Cell suspension was added into 96-well plate with 50 µl per well ($5\times10^5$ cells/well). There are three parallel samples per group.
8. Addition of stimulator: The stimulator was formulated into a medium (50 ul of medium contains 0.1 ul of PMA=0.2 µg/ml, 0.1 ul of ionomycin=2 µg/ml) having a concentration twice of the final concentration by using complete medium (The final concentration of anti-CD3 was 2 µg/ml, anti-CD28 was 0.1 µg/ml), and antigen stimulator was 10 µg/ml;

9. The cells were incubated at 37° C. for 72 hours, and measured by flow cytometry. CD8 antibody can be stained before the measurement.

The result was analyzed by t-test for statistical analysis. p<0.05 indicates significant difference and p<0.01 indicates very significant difference.

Figure 6:
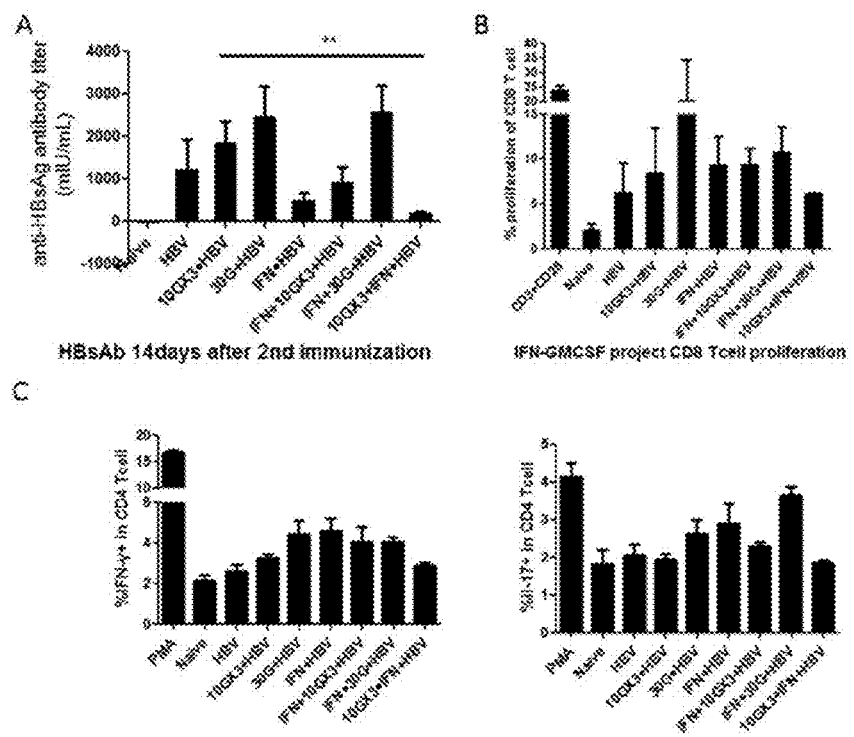
FIG. 6 shows A. the total IgG of vaccination with antiviral agent IFN-α 2a, recombinant human granulocyte macrophage colony stimulating factor in combination with hepatitis B vaccine to increase immune response of hepatitis B vaccine in embodiment 3 as measured by ELISA; B. the measurement results of the T lymphocytes amplification by vaccination with antiviral agent IFN-α 2a, recombinant human granulocyte macrophage colony stimulating factor in combination with hepatitis B vaccine to increase immune response of hepatitis B vaccine in embodiment 3; IL-17 and IFN-γ expression in CD4 T cells vaccinated by antiviral agent IFN-α 2a, recombinant human granulocyte macrophage colony stimulating factor in combination with hepatitis B vaccine to increase immune response of hepatitis B vaccine in embodiment 3 as measured by flow cytometry.

Results Show That:

1. Hepatitis B surface antigen was measured by ELISA on day 14 after the $2^{nd}$ immunization. It is found that (FIG. 6-A) the injection of IFN-α1b one day before the injection of HBV vaccine can significantly decrease the level of antibody against hepatitis B surface antigen compared to the control group. Especially, the level of humoral immunity was significantly inhibited in the group with co-administration of IFN-α1b and hepatitis B vaccine. It is demonstrated that administration of Type I interferon one day before or with the injection of hepatitis B vaccine can affect the humoral immune level of hepatitis B vaccine.

2. By CFSE method measuring T cells proliferation (FIG. 6-B) and flow cytometer measuring intracellular staining of IFN-γ, IL-17 in CD4 T cells (FIG. 6-C), it is found that the effect of interferon on the immune response of CD8 cells induced by GM-CS in combination with recombinant hepatitis B vaccine was not significant.

Embodiment 5

Figure 7:
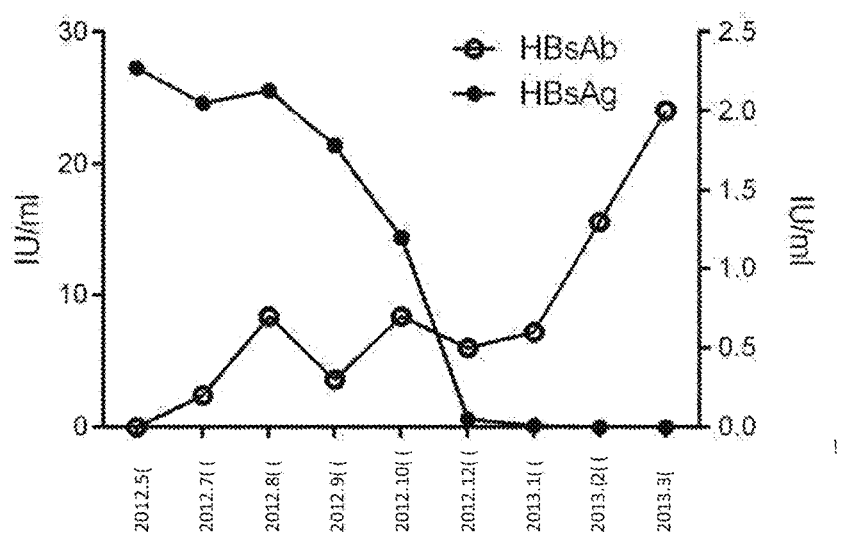
FIG. 7 shows the decrease of HBsAg level in embodiment 5, wherein the ordinate represents the level of HBsAg (IU/ml), and the abscissa represents the time (May 2012-March 2013).

Evaluation of the clinical efficacy of chronic hepatitis B patient treated with the immune strategy of antiviral agent, interferon, and GM-CSF in combination of hepatitis B vaccine 56 years old male patient, whose mother was positive in HBsAg, was diagnosed as HBeAg positive chronic hepatitis B in May 2004, and has been treated with entecavir since May 2009. HBeAg seroconversion was observed two years later. From May 2012, in addition to entecavir, the patient began to receive combinatorial treatment of polyethylene glycol interferon α-2a subcutaneously injected at a dosage of 180 µg/week. At the $1^{st}$, $2^{nd}$, $3^{rd}$, $6^{th}$, $9^{th}$ and $12^{th}$ month of the interferon treatment, an immune intervention using granulocyte-macrophage colony stimulating factor (GM-CSF) and hepatitis B vaccine was administrated to the patient, in which 2-3 days after the injection of the interferon, 75 µg of GM-CSF was intramuscularly injected once a day for three consecutive days, and 20 µg of hepatitis B vaccine was injected once at the same site on the fourth day. From August 2012, i.e. 3 months after the initiation of interferon treatment, Entecavir treatment was discontinued. As shown in FIG. 7, from December 2012, i.e. 7 months after the initiation of interferon treatment, the patient became HBsAg negative and showed increasing level of anti-HBsAg antibody.

INDUSTRY APPLICATION

The Advantages of the Present Disclosure are:

1. Compared to the existing technology, antiviral agent is used in the pharmaceutical composition of present disclosure to temporarily inhibit virus replication, then immune modulator plus vaccine are used for immunization, which can effectively enhance the immune response of hepatitis B vaccine, avoid the lacking of response caused by drug resistance of mono antiviral drug, and lead a new direction for treatment of chronic HBV infection.

2. As indicated in embodiments 1-3, compared with the existing antiviral therapy, the immune combination of antiviral agents in present disclosure can effectively stimulate the level of humoral and cellular immunity, and significantly enhance immune response.

3. The pharmaceutical composition in present disclosure is convenient to be used, less costly, has minimal side effect, and is easy to be popularized.

4. The pharmaceutical composition in present disclosure can not only break the antibody response stimulated by immune tolerance, stimulate the CD4+ and CD8+ T cell response of organism including the stimulation of Th1, Th2, Th17, Tc1 and Tc17, clear virus effectively by immune responses, but also prevent recurrence of infection after curation.

We claim:

1. A method of overcoming host immune tolerance in a subject having chronic hepatitis B virus (HBV) infection, comprising administering to the subject a first antiviral agent, wherein the first antiviral agent is polyethylene glycol-IFN-α 2a capable of providing sustained release, an immunomodulatory agent of recombinant human granulocyte macrophage colony stimulating factor (rhGM-CSF) and a recombinant HBV vaccine, such that the immune tolerance of the chronic HBV infection in the subject is overcome, wherein the immunomodulatory agent is administered once per day for three consecutive days in total for each immunization with the recombinant HBV vaccine prior to the administration of the recombinant HBV vaccine.

2. The method of claim 1, wherein the immune tolerance is overcome such that the HBsAg in serum is substantially reduced or becomes negative with the appearance of anti-HBsAg antibody in the subject.

3. The method of claim 1, wherein the recombinant HBV vaccine is a subunit protein vaccine or a therapeutic HBV vaccine.

4. The method of claim 1, wherein the first antiviral agent is administered regularly over a course of treatment.

5. The method of claim 4, wherein the course of treatment for the first antiviral agent is at least 3, 6, 8, 10, 12 months, or longer.

6. The method of claim 5, wherein the immunomodulatory agent and the recombinant HBV vaccine are administered about 4 to about 12 times for every 12 months at intervals of at least 1 month.

7. The method of claim 5, wherein each of the immunomodulatory agent and the recombinant HBV vaccine are administered 4 to about 12 times for every 12 months, at varied intervals ranging from 1 month to 3 months.

8. The method of claim 1, further comprising administering a second antiviral agent which is different from the first antiviral agent.

9. The method of claim 8, wherein the second antiviral agent is a nucleos(t)ide analog, or an agent that can inhibit life cycle of HBV.

10. The method of claim 8, wherein both the first and the second antiviral agents are administered regularly over a course of treatment.

11. The method of claim 8, wherein the second the antiviral agent is a nucleos(t)ide analog or another agent that can inhibit life cycle of HBV, and wherein the first and the second antiviral agents are co-administered for over a course of treatment.

12. The method of claim 8, wherein the second the antiviral agent is a nucleos(t)ide analog or another agent that can inhibit life cycle of HBV, and wherein the first and the second antiviral agents are co-administered for around 3 months before the administration of the second antiviral agent is discontinued while the administration of the first antiviral agent continues.

13. The method of claim 11, wherein each of the immunomodulatory agent and the recombinant HBV vaccine are administered about 4 to about 12 times for every 12 months at intervals of at least 1 month.

14. The method of claim 1, further comprising administering a second antiviral agent which is different from the first antiviral agent.

15. The method of claim 1, wherein the first antiviral agent is administered prior to administration of the recombinant HBV vaccine and the immunomodulatory agent is administered prior to administration of the recombinant HBV vaccine.

16. The method of claim 1, wherein the recombinant HBV vaccine and the recombinant human granulocyte macrophage colony stimulating factor GM-CSF have a weight ratio of 1:1-30.

\* \* \* \* \*

UNITED STATES PATENT AND TRADEMARK OFFICE
CERTIFICATE OF CORRECTION

PATENT NO. : 10,086,067 B2
APPLICATION NO. : 15/007160
DATED : October 2, 2018
INVENTOR(S) : Bin Wang et al.

Page 1 of 1

It is certified that error appears in the above-identified patent and that said Letters Patent is hereby corrected as shown below:

In the Specification

Column 4, Line 5, "Serpelloni" should be -- Serpelloni G, --.

Signed and Sealed this
Sixth Day of November, 2018

Andrei Iancu
*Director of the United States Patent and Trademark Office*